United States Patent [19]

Della Bella et al.

[11] Patent Number: 4,575,506

[45] Date of Patent: Mar. 11, 1986

[54] METHOD OF TREATMENT FOR INHIBITING THE TOLERANCE ONSET WHILE TREATING PAINFUL SYNDROMES WITH CENTRAL ANALGESICS

[75] Inventors: Davide Della Bella, Milan; Viviana Frigeni, Monza Mi; Angelo Carenzi, Busto Arsizio, all of Italy

[73] Assignee: Zambon S.p.A., Vicenza, Italy

[21] Appl. No.: 667,441

[22] Filed: Nov. 1, 1984

[30] Foreign Application Priority Data

Nov. 3, 1983 [IT] Italy ................................. 23571 A/84

[51] Int. Cl.$^4$ .................... A61K 31/44; A61K 31/165
[52] U.S. Cl. ...................................... 514/282; 514/619
[58] Field of Search ................ 424/260, 324; 514/282, 514/619

[56] References Cited

PUBLICATIONS

Chem. Abst., 87-111572D, (1977).

Primary Examiner—Stanley J. Friedman
Attorney, Agent, or Firm—Cushman, Darby & Cushman

[57] ABSTRACT

Thiamphenicol for use in the inhibition of tolerance onset while treating painful syndromes with central analgesics.

7 Claims, No Drawings

METHOD OF TREATMENT FOR INHIBITING THE TOLERANCE ONSET WHILE TREATING PAINFUL SYNDROMES WITH CENTRAL ANALGESICS

DESCRIPTION

This invention relates to the use of thiamphenicol for inhibiting the tolerance onset while treating painful syndromes with central analgesics.

Thiamphenicol (Merck Index, X ed., pag. 1332) is known since many years as antibacterial agent.

It has now been found that thiamphenicol inhibits the tolerance onset while treating painful syndromes with central analgesics.

It is known that recurring adminstrations of central analgesics cause a number of side-effects.

One of these side-effects is the onset of tolerance to the effects of the drug, phenomenon which requires an increase of the doses which are administered to obtain the desired analgesic effect.

Schematically, the medium-long term treatment with central analgesics may be divided into three periods: the period of the tolerance onset at the beginning of the treatment, the presence of the tolerance during the treatment and the period of the disappearance of the tolerance after the interruption of the treatment.

This phenomenon is particularly evident in case of morphine.

In case of other central analgesics such as pentazocine, meperidine, methadone and laevorphanol, this phenomenon generally occurs in a similar way even if sometimes is less severe.

Furthermore, it is known that chloramphenicol (Merck Index, 10th edition ed., pag. 289), which is an antibacterial agent structurally very similar to thiamphenicol, inhibits the restoration of the normal sensibility of the animal body also after the interruption of the treatment with an analgesic agent whereas it does not modify the tolerance onset.

It was therefore completely unexpected that thiamphenicol could inhibit the tolerance onset.

The ability of thiamphenicol to inhibit the tolerance onset induced by morphine in mice is shown in the following table.

| Pretreatment 4 days | Challenge after 5 days 5 mg/kg/sc* | Latency time (seconds) |
| --- | --- | --- |
| physiological solution | morphine | 20,46 + 1,40 |
| morphine (5 mg/kg/sc*/2 times a day) | morphine | 11,50 + 0.78 |
| thiamphenicol (50 + mg/kg/os/2 times a day) morphine (5 + 5 mg/kg/sc/2 times a day) | morphine | 20,00 + 1,52 |
| thiamphenical (50 + 50 mg/kg/os/2 times a day | morphine (P 0,001) | 20,50 + 1.33 |

*subcutaneously

Furthermore, in the animals treated with morphine alone until tolerance was induced, the addition of thiamphenicol to morphine showed a progressive reappearance of the analgesic effect of morphine.

The analgesic activity has been evaluated with the hot plate test.

The analgesic activity has been expressed as latency time 20 minutes after administration of the challenge of morphine.

Each group was comprising 40 animals.

$P<0.001$ with respect to the group of animals treated for 4 days with morphine alone.

In view of the fact that the time necessary for the tolerance onset and that the degree of the latter varies from analgesic to analgesic, the dose of thiamphenicol will be set having regard to the condition of the patient and to the dose and the type of the central analgesic which is administered to the patient. Thus a patient can receive a dose comprised between 1 mg and 15 mg for each mg of the administered analgesic.

Having regard to the pharmaceutical forms which one desires to use, thiamphenicol can be replaced with a suitable derivative thereof which releases thiamphenicol in the treated animal body. Examples of such derivatives are thiamphenicol glycinate hydrochloride, thiamphenicol palmitate and thiamphenicol succinate. The doses of such products will be generally set by taking into consideration the amount of thiamphenicol which they release in the treated body and the time required to release said amount. For human use thiamphenicol or a derivative thereof is administered as a pharmaceutical form.

The active ingredient may be alone or associated with central analgesic agents. This type of association is preferred in case of injectable forms.

These compositions can contain the active ingredient or ingredients together with organic or inorganic, solid or liquid pharmaceutical excipients and can be suitable for oral or parenteral administration.

The finished pharmaceutical forms may be solid such as tablets, sugar-coated tablets, capsules, powders and granules, or liquid such as solutions, suspensions and emulsions.

They can also be prepared in such a way that the release of the drug after administration is sustained. In addition they can contain also preservatives, stabilizers, humidifying agents, emulsifiers, salts to regulate the osmotic pressure, buffers, coulering agents, flavoring agents, etc.

The pharmaceutical compositions according to this invention are prepared by conventional techniques which comprise granulating and tableting or dissolving and sterilizing the ingredients in accordance with the desired pharmaceutical form.

Said compositions may be administred whenever is necessary to treat painful syndromes by recurring administration of analgesics which cause tolerance.

We claim:

1. A method of inhibiting tolerance onset in the treatment of painful syndromes with a central analgesic agent comprising admistering to a patient thiamphenicol or a derivative of thiamphenicol which releases thiamphenicol in the body in association with the central analgesic agent and an amount effective to inhibit the tolerance onset of the central analgesic agent, the central analgesic agent being morphine, pentazocine, meperidine, methadone or laevorphanol.

2. A method according to claim 1 wherein there is employed thiamphenicol.

3. A method according to claim 1 wherein there is employed a derivative of thiamphenicol which releases thiamphenicol in the body.

4. A method according to claim 1 wherein there is administered 1 to 15 mg of thiamphenicol for each milligram of the central analgesic agent.

5. A method according to claim 1 wherein there is employed morphine.

6. A composition suitable to inhibit tolerance onset in the treatment of painful syndromes with a central analgesic agent comprising (1) thiamphenicol or a thiamphenicol derivative which releases thiamphenicol in the body in an amount effective to inhibit the tolerance onset and (2) a central analgesic agent which is morphine, pentazocine, meperidine, methadone or laevorphanol and wherein there is present 1 to 15 mg of thiamphenicol for each milligram of the central analgesic agent.

7. A composition according to claim 6 wherein the central analgesic agent is morphine.

* * * * *